United States Patent [19]
Kukal et al.

[11] Patent Number: 5,804,444
[45] Date of Patent: Sep. 8, 1998

[54] HYPOTHERMIC STORAGE TECHNOLOGY FOR BIOLOGICAL MATERIAL

[75] Inventors: Olga Kukal; Thomas F. Allen, both of Wolfville, Canada

[73] Assignee: Tolix Holdings Limited, Dartmouth, Canada

[21] Appl. No.: 731,210

[22] Filed: Oct. 10, 1996

[51] Int. Cl.$^6$ .............. C12Q 1/02; C12Q 1/00; A23B 4/00; A23L 1/00
[52] U.S. Cl. .............. 435/374; 435/4; 435/29; 426/393; 426/524; 426/665
[58] Field of Search .............. 435/374, 4, 29; 426/665, 393, 524

[56] References Cited

U.S. PATENT DOCUMENTS

| | | | |
|---|---|---|---|
| 3,637,405 | 1/1972 | Mendelson et al. | 426/2 |
| 3,991,218 | 11/1976 | Earle et al. | 426/264 |
| 4,387,109 | 6/1983 | Kahn et al. | 426/321 |
| 4,555,410 | 11/1985 | Yamane | 426/384 |
| 4,565,643 | 1/1986 | Arai et al. | 252/70 |
| 4,587,027 | 5/1986 | Preusch et al. | 252/73 |
| 4,601,842 | 7/1986 | Caple et al. | 252/70 |
| 4,772,480 | 9/1988 | Yamane | 426/327 |
| 4,832,972 | 5/1989 | Toledo-Flores et al. | 426/327 |
| 4,895,729 | 1/1990 | Powrie et al. | 426/316 |
| 5,269,149 | 12/1993 | Zeidler | 62/78 |
| 5,310,427 | 5/1994 | Manome | 119/201 |
| 5,403,609 | 4/1995 | Subotics et al. | 426/524 |

FOREIGN PATENT DOCUMENTS

| | | | |
|---|---|---|---|
| 63-263440 | 10/1988 | Japan | G01N 1/28 |
| 95/16201 | 6/1995 | WIPO | G01N 33/04 |

OTHER PUBLICATIONS

Sealand, Shipping Guide for Perishables 1991.
Wilen, et al., Dispersion–force effects in interfacial premelting of ice, Physical Reviews B, vol. 52, issue 16, pp. 12,426–12,433, 1995.
Roos, Y. J. Food Sci, vol. 51 (3), pp. 684–686, 1986.
Wang et al. J. Food Sci. vol. 56 (2), pp. 302–308, 1991.
Alasalvar et al. J. Food Sci. vol. 60 (3), pp. 619–621, 1995.
Hastings et al. J. Food Sci. vol. 50, pp. 503–503, 1985.
Love, R. Freezing Irradiat. Fish., Proc. Conf., Abstract, 1967.
Chen et al. Int. J. Food Sci. & Tech. vol. 30 (2), pp. 167–173, Abstract enclosed, 1995.
Bonnet et al. Int. J. Food Sci. & Tech. vol. 27 (4), pp. 399–408, Abstract enclosed, 1992.
Shjga et al. J. Food Sci. vol. 53 (4), pp. 1076–1080, Abstract enclosed, 1988.

*Primary Examiner*—Leon B. Lankford, Jr.
*Assistant Examiner*—Christopher R. Tate
*Attorney, Agent, or Firm*—Fulbright & Jaworski, LLP

[57] ABSTRACT

The present invention relates to the optimum bio-storage temperature of biological materials. The temperature is between the melting point depression of the biological material and zero degrees C. The melting point depression temperature is determined by thermography, differential scanning calorimetry and cryomicroscopy.

19 Claims, 3 Drawing Sheets

HYPOTHERMIC STORAGE TECHNOLOGY FOR BIOLOGICAL MATERIAL

This invention relates to methods of preservation of biological material for extended periods. Additionally, the invention relates to methods of determining the optimum temperature at which to store biological materials for extended periods.

BACKGROUND OF THE INVENTION

It is known in the art that biological material can be stored at reduced temperatures to decrease the rate of deterioration of the biological material. The low temperature inhibits the activity of degradation enzymes in the biological material as well as inhibiting the growth of microorganisms which degrade the material. Currently available technologies can be divided into two categories. The first category includes storage of the material in an unfrozen state. Customarily, the biological material is stored at temperatures between 0° C. and 10° C. The second category of storage includes storage of the biological material in a frozen state. Customarily, the material is stored at a temperature of −15° C. or less.

The existing technologies suffer from serious defects. Storage of biological material at temperatures between 0° C. and 10° C. extends the usable lifetime of the material. However, the extension is of a limited duration. Generally, biological material begins to undergo a noticeable amount of deterioration in one or two days and becomes completely unusable after two or more days. This places major constraints on the availability of fresh materials such as foodstuffs and other biological materials. The materials must be produced close enough to the location at which they will be sold so that an adequate usable life time remains after shipping.

Freezing of material overcomes some of the difficulties inherent in shipping fresh materials. Once frozen, the material may be stored for protracted periods and shipped over long distances. In the process of freezing, the formation of ice crystals within the material results in damage to the material, which reduces the quality of the material. The reduction in the quality of material stored in the frozen state results in a reduction in the value of the material relative to the fresh, unfrozen state.

Thus, there is a need in the art to provide a method for the extended storage of biological material with no loss of the usability or quality of the material. Such a method would find broad applicability, for example, in the handling of foodstuffs, cut flowers, cells, tissues, gametes, organs, and whole organisms. The present invention will be useful in the handling of all types of foodstuffs. The present invention is particularly useful for the storage of fresh produce, such as carrots, mushrooms, apples, onions, kiwis, citrus fruits, broccoli, tomatoes, and garlic. The present invention is equally useful for the storage of fresh caught seafood, such as shrimp, scallops, tuna, salmon, lobster, crab, oysters, and other fresh caught fish. The present invention is also useful for the storage of meat, such as chicken, beef, pork, lamb, and other types of meat. The invention is particularly suited for prepared cuts of meat, such as steaks, chicken breasts, hamburger, and fish fillets. The invention may also be used to store whole carcasses for shipping.

SUMMARY OF THE INVENTION

One object of the invention is to provide a methodology for determining the optimum bio-storage temperature of biological materials. This method includes the step of determining the melting point depression of the material to be stored.

An object of the invention is to provide a method of storage of biological materials comprising the steps of determining the melting point depression of the biological material and storing the biological material at a temperature greater than the melting point depression and less than 0° C.

DETAILED DESCRIPTION OF THE INVENTION

This invention relates to the optimum storage conditions for biological material. Storage at lower than ambient temperature results in a decrease in the rate of deterioration of biological materials. This decrease is caused by inhibition of degradation enzymes in the biological material, as well as a decrease in the growth rate of microbial contaminants. While it is possible to virtually completely halt the deterioration of biological material caused by degradation enzymes and microbes by freezing the material, such freezing results in a concomitant degradation of the material as a result of formation of ice within the cells of the material and subsequent rupture of the cells. The present invention provides a method for determining the optimum bio-storage temperature of a biological material, i.e., the lowest temperature at which the material may be kept without danger of freezing.

In order to determine the appropriate bio-storage temperature for biological material, a detailed analysis of the melting point of the material is required. This is accomplished by means of extremely accurate thermography or differential scanning calorimetry and visually confirmed by cryomicroscopy.

The melting point of pure water is 0° C. Biological materials, by virtue of the presence of solute molecules such as ions, proteins, etc., generally will have a melting point that is lower than 0° C. The difference between 0° C. and the observed melting point is the melting point depression of the biological material. The optimum bio-storage temperature is the temperature as close to, but greater than, the melting point depression as is reliably attainable by current refrigeration technology. At present, this temperature is approximately 0.1° C. greater than the melting point depression.

EXAMPLE 1

Determination of the melting point depression

Figure 1:
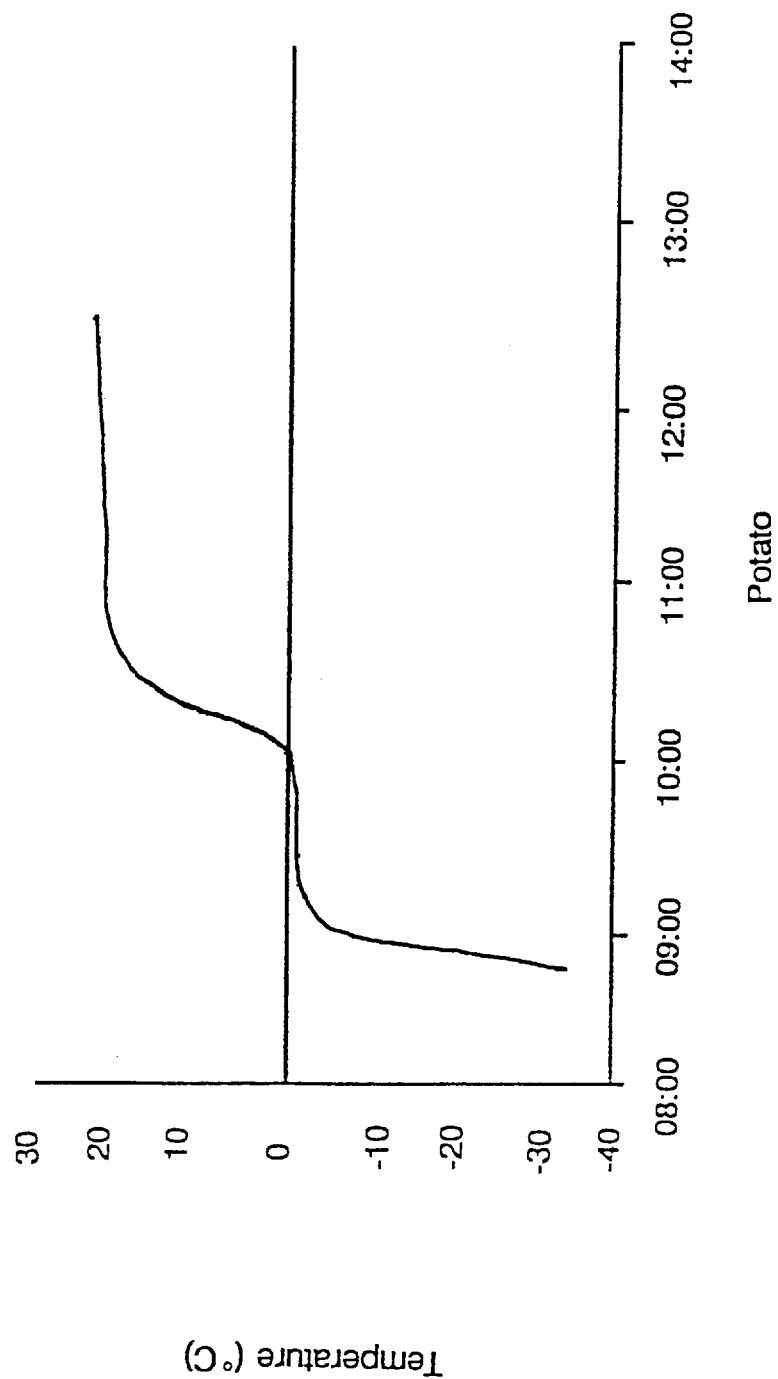
FIG. 1 is a plot of the temperature of a potato sample as a function of time determined by thermography.
Figure 3:
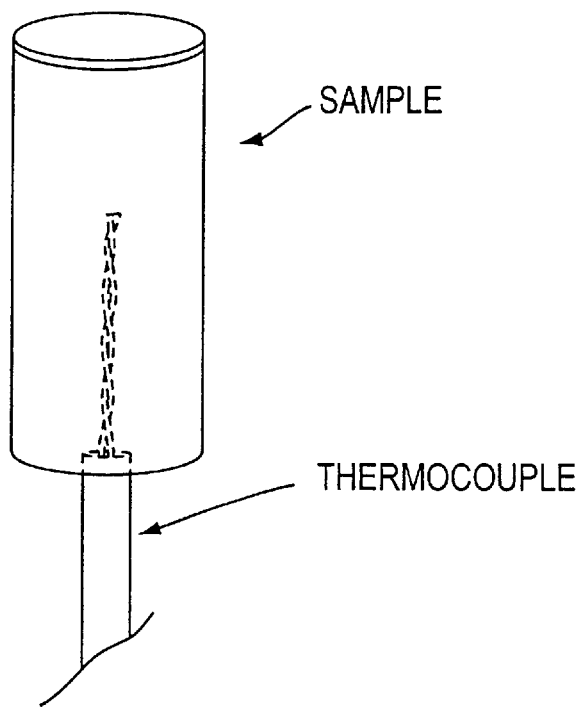
FIG. 3 is a schematic diagram of the arrangement of a tissue sample prepared for thermography.

A 0.5 gram cylindrical tissue section is removed from the biological material. Type J thermocouples are inserted longitudinally into the center of the tissue section as shown in FIG. 3. The tissue sections are then placed inside Corning cryovials (3 Ml). The samples are then placed into an ultra-low temperature bath set at −30° C., and the freezing exotherm is recorded. The thermocouples are connected to an eight-channel National Instruments Virtual Instrument (VI) configured for thermography. Initial signal processing and linearization are accomplished by an analog device's isolated linearized type J thermocouple input on a National Instruments back-plane. Three samples are run simultaneously from each biological material. After the samples equilibrate to −30° C., the temperature in the bath is raised at 1° C. per minute to 10° C. The onset of melting temperature may be determined from the plot of temperature of the tissue sample versus time or, alternatively, from the data string by Fourier transformation or other known data analysis techniques. A representative example of the type of data obtained using this methodology is shown in FIG. 1.

EXAMPLE 2

Melting point depression determination by differential scanning calorimetry (DSC)

Figure 2:
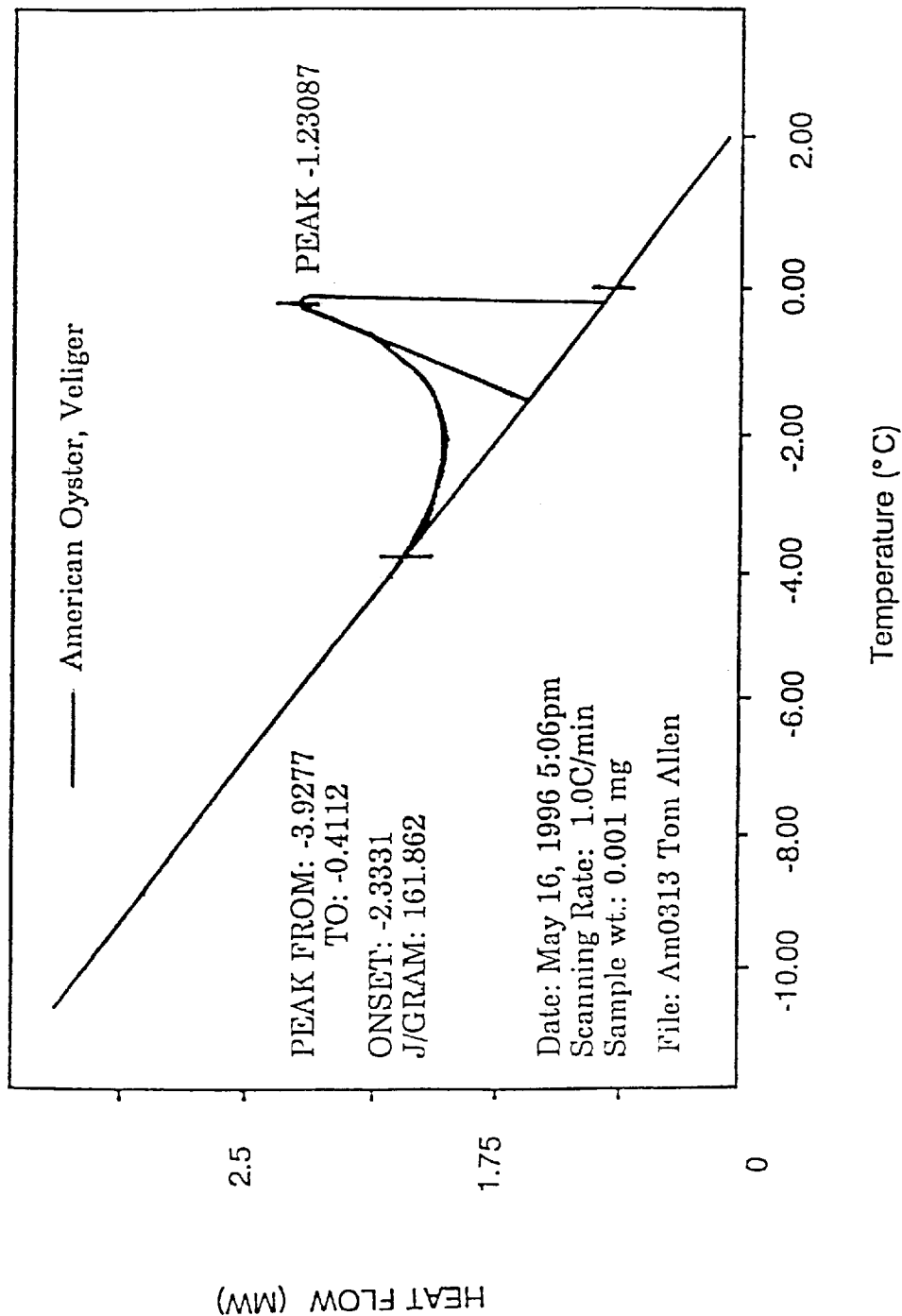
FIG. 2 is a plot of the heat flow as a function of temperature in American oysters determined by differential scanning calorimetry.

One individual is weighed and placed into a sample container, and the container is sealed. The specimen is placed in the sample side of the differential scanning calorimeter. The sample is cooled at 20° C. per minute to −30° C., and then is warmed at 1° C. per minute to 10° C. The heat flow into the sample as a function of the temperature of the sample is measured. As the sample approaches the melting point, there is an increase in the heat flow required to raise the temperature a given amount. This increase is a result of the fact that energy is required to change the state of the material from the solid state (frozen) to the liquid state (melted). A representative thermogram is presented in FIG. 2. With currently available technology, this technique permits the determination of the melting point depression to within a few ten thousandths of a degree C.

EXAMPLE 3

Melting point depression confirmation by isothermal cryomicroscopy

A 0.2 mm thick (frozen) thin section of tissue is taken from the sample to be analyzed. The section is placed inside a quartz crucible and covered with a cover slip. The crucible is placed inside a Linkam BCS 196 Cryostage on an Olympus BH2 microscope. The stage of the microscope is controlled by a Linkam TMS 92 controller, LNP2 pump and interfaced to a P5 90 MHz computer using Linkam link 2 software running under windows 3.1. The sample is examined visually for shifts in the crystal lattice for 80 minutes at and below the onset temperature determined by thermography. The magnification of the microscope is set to 200X. The sample is cooled to −30° C. at a rate of 20° C. per minute. If necessary, the microscope stage may be opened and freezing may be nucleated. The sample is held at −30° C. for 5 minutes, and then is warmed at 10° C. per minute to a temperature approximately 2° C. below the onset temperature determined by thermography. The sample is then warmed at 1° C. per minute to a temperature approximately 1° C. below the onset temperature determined by thermography. The sample is then warmed at 0.1° C. per minute to a temperature 0.1° C. lower than the onset temperature determined by thermography. The sample is held at this temperature for 80 minutes. An ice crystal is identified by visual inspection and a micrometer is set to one edge of the crystal. The crystal is then checked at five-minute intervals to see if the edge of the crystal is receding. If there is no movement in the crystal edge, then the sample is warmed at a rate of 0.1° C. per minute to a temperature equal to the onset temperature determined by thermography. The sample is once again held for 80 minutes with a micrometer set to the edge of an ice crystal and checked at five-minute intervals to see if the edge of the crystal is moving. If no movement is observed, then the sample is again warmed 0.1° C. per minute to a temperature 0.1° C. greater than the onset temperature, and the holding procedure repeated with visual inspection of the ice crystal at five-minute intervals. This procedure allows the visual confirmation of the melting point depression determined by thermography and/or differential scanning calorimetry.

EXAMPLE 4

Using thermography and cryomicroscopy, the melting point depression and, hence, the optimum bio-storage temperature has been determined for a number of types of biological material. The data is presented in Table 1.

TABLE 1

| Material | Melting Point | Currently Attainable Bio-storage Temperature |
|---|---|---|
| Tiger Shrimp | −0.4 | −0.3 |
| Sea Scallop Meat | −3.4 | −3.3 |
| Chicken Breast | −1.2 | −1.1 |
| Carrot | −2.1 | −2.0 |
| Blue Fin Tuna | −3.3 | −3.2 |
| Atlantic Salmon | −4.2 | −4.1 |
| American Lobster | −5.2 | −5.1 |
| Dungeness Crab | −2.5 | −2.4 |
| Bay Scallops Meat | −4.4 | −4.3 |
| American Oyster Meat | −2.3 | −2.2 |
| Belon Oyster Meat | −3.9 | −3.8 |
| Wing Steak (Beef) | −1.8 | −1.7 |
| Mushroom (white) | −1.6 | −1.5 |
| Hamburger (extra lean) | −2.0 | −1.9 |
| Apple (Granny Smith) | −2.1 | −2.0 |
| Onion (white pearl) | −1.2 | −1.1 |
| Kiwi | −2.9 | −2.8 |
| Pork Chop | −1.8 | −1.7 |
| Lemon | −2.1 | −2.0 |
| Orange | −2.1 | −2.0 |
| Broccoli | −1.2 | −1.1 |
| Tomato (Roma) | −2.0 | −1.9 |
| Garlic | −2.0 | −1.9 |

As indicated in Table 1, it is currently envisioned that the optimum bio-storage temperature of biological materials is a temperature approximately 0.1° C. higher than the melting point depression temperature. It is envisioned that, as temperature control technology provides greater accuracy and precision of temperature, the optimum bio-storage temperature will be closer to the melting point depression temperature. One skilled in the art will readily appreciate that the optimum bio-storage temperature may be closer to the melting point depression temperature than 0.1° C. The limiting factor will be the ability of the temperature control technology to accurately and precisely produce a temperature that remains somewhat above the melting point depression temperature. Current technology permits a temperature of 0.1° C. greater than the melting point depression temperature. As the technology improves, the optimum bio-storage temperature may decrease to 0.05° C. or even 0.01° C. greater than the melting point depression temperature.

Although the present invention is described in terms of preferred embodiments of biological materials, it is understood that the melting point depression can be determined for any biological material, and thus the optimum bio-storage temperature can be determined for any biological material. Accordingly, it is intended that the appended claims include all such materials and equivalents which come within the scope of the invention as claimed.

We claim:

1. A method for determining an optimum bio-storage temperature of a biological material, comprising the steps of:

selecting a biological material from the group consisting of food and non-food materials; and determining a melting point depression of the biological material, wherein the optimum bio-storage temperature is greater than the melting point depression and equal to or less than 0° C.

2. A method according to claim 1, wherein the biological material is selected from the group consisting of meat, fish and produce.

3. A method according to claim 2, wherein the biological material is meat.

4. A method according to claim 2, wherein the biological material is fish.

5. A method according to claim 2, wherein the biological material is produce.

6. A method for storing biological material, comprising the steps of:

selecting a biological material from the group consisting of food and non-food material;

determining a melting point depression of the biological material; and maintaining the biological material at an optimum bio-storage temperature, wherein said optimum bio-storage temperature is a temperature greater than the melting point depression of said biological material and equal to or less than 0° C.

7. A method according to claim 6, wherein the biological material is a food.

8. A method according to claim 7, wherein the biological material is selected from the group consisting of meat, fish, shellfish and produce.

9. A method according to claim herein the biological material is meat.

10. A method according to claim 9, wherein the biological material is chicken breast and the chicken breast is maintained at a temperature greater than −1.2° C and less than 0° C.

11. A method according to claim 9, wherein the biological material is beef steak and the beef steak is maintained at a temperature greater than −1.8° C. and less than 0° C.

12. A method according to claim 8, wherein the biological material is fish.

13. A method according to claim 12, wherein the biological material is blue fin tuna and the blue fin tuna is maintained at a temperature greater than −3.3° C. and less than 0° C.

14. A method according to claim 12, wherein the biological material is Atlantic salmon and the Atlantic salmon is stored at a temperature greater than −4.2° C. and less than 0° C.

15. A method according to claim 8, wherein the biological material is American lobster and the American lobster is stored at a temperature greater than −5.2° C. and less than 0° C.

16. A method according to claim 8, wherein the biological material is sea scallop meat and the sea scallop meat is stored at a temperature greater than −3.4° C. and less than 0° C.

17. A method according to claim 8, wherein the biological material is produce.

18. A method according to claim 17, wherein the biological material is kiwi and the kiwi is stored at a temperature greater than −2.9° C. and less than 0° C.

19. A method according to claim 17, wherein the biological material is an apple and the apple is stored at a temperature greater than −2.1° C. and less than 0° C.

* * * * *